United States Patent
Liu et al.

(10) Patent No.: US 12,370,050 B2
(45) Date of Patent: Jul. 29, 2025

(54) HIP PROSTHESIS CONTAINING ZIRCONIUM-NIOBIUM ALLOY ON OXIDATION LAYER AND PREPARATION METHOD THEREOF

(71) Applicant: Just Medical Devices (Tianjin) Co., Ltd., Tianjin (CN)

(72) Inventors: Nian Liu, Tianjin (CN); Jinduo Ye, Tianjin (CN); Haoqiang Ti, Tianjin (CN); Hongxiu Zhou, Tianjin (CN)

(73) Assignee: Just Medical Devices (Tianjin) Co., Ltd., Tianjin (CN)

( * ) Notice: Subject to any disclaimer, the term of this patent is extended or adjusted under 35 U.S.C. 154(b) by 238 days.

(21) Appl. No.: 17/907,795

(22) PCT Filed: Jun. 21, 2021

(86) PCT No.: PCT/CN2021/101277
§ 371 (c)(1),
(2) Date: Aug. 29, 2022

(87) PCT Pub. No.: WO2022/088701
PCT Pub. Date: May 5, 2022

(65) Prior Publication Data
US 2023/0248527 A1    Aug. 10, 2023

(30) Foreign Application Priority Data

Oct. 30, 2020   (CN) .......................... 202011195096.3

(51) Int. Cl.
*A61F 2/30*    (2006.01)
(52) U.S. Cl.
CPC ...................... *A61F 2/3094* (2013.01); *A61F 2002/30011* (2013.01); *A61F 2002/30971* (2013.01)

(58) Field of Classification Search
CPC ............... A61L 27/306; A61L 2400/18; A61L 2430/02; A61L 27/047; A61L 27/50; A61L 2430/24; Y02P 10/25; B22F 5/10; B22F 3/15; B22F 3/24; B22F 10/64;
(Continued)

(56) References Cited

U.S. PATENT DOCUMENTS

2016/0305005 A1* 10/2016 Walker .................. A61F 2/3609
2018/0177597 A1    6/2018 Chung et al.

FOREIGN PATENT DOCUMENTS

| CN | 106236328 A | 12/2016 |
|----|-------------|---------|
| CN | 106618804 A | 5/2017 |
| CN | 112404431 A | 2/2021 |

(Continued)

OTHER PUBLICATIONS

International Search Report of PCT/CN2021/101277.
Written Opinion of PCT/CN2021/101277.
(Continued)

*Primary Examiner* — Ricardo D Morales

(57) ABSTRACT

The present disclosure discloses the hip prosthesis containing zirconium-niobium alloy on oxidation layer and a preparation method thereof, the hip prosthesis comprises a femoral stem, a femoral head, liners and a shell; the shell and femoral stem are prepared by using zirconium-niobium alloy powder as a raw material, and performing Sinter-HIP, cryogenic cooling and surface oxidation; the prepared shell and femoral stem are provided with partitioned trabeculae and formed by 3D printing. The problem of traditional manufacturing methods cannot process complex structures and failure of connection between sleeve and femoral handle is solved by 3D printing technology. Meanwhile, the preparation method can improve the bonding strength between trabecular bone and solid, and improve the service life of prosthesis.

10 Claims, 16 Drawing Sheets

(58) Field of Classification Search
CPC .......... B22F 2998/10; B22F 3/11; B22F 2003/247; B22F 2003/248; B22F 7/002; B22F 7/008; B22F 10/66; B33Y 40/20; B33Y 80/00; C22C 16/00; C22C 1/0458; C22F 1/186; C22F 1/02; A61F 2/3609; A61F 2002/3006; A61F 2002/3611; A61F 2/3094; A61F 2002/30011; A61F 2002/30971; A61F 2/30767; A61F 2002/30004; A61F 2002/3092; A61F 2/3662; A61F 2002/3401; A61F 2002/3403; A61F 2002/365; A61F 2310/00485; A61F 2310/00491; A61F 2/32; A61F 2/34; A61F 2/36; A61F 2002/30985; C21D 9/0068
See application file for complete search history.

(56) References Cited

FOREIGN PATENT DOCUMENTS

| | | | |
|---|---|---|---|
| EP | 0437079 | A1 | 7/1991 |
| EP | 3698902 | A1 | 8/2020 |

OTHER PUBLICATIONS

M.B. Sedelnikova et al., "Comparative investigations of structure and properties of micro-arc wollastonite-calcium phosphate coatings on titanium and zirconium-niobium alloy", Bioactive Materials, Feb. 13, 2017.

\* cited by examiner

HIP PROSTHESIS CONTAINING ZIRCONIUM-NIOBIUM ALLOY ON OXIDATION LAYER AND PREPARATION METHOD THEREOF

CROSS-REFERENCE TO RELATED APPLICATIONS

This Application is a national stage application of PCT/CN2021/101277. This application claims priorities from PCT Application No. PCT/CN2021/101277, filed Jun. 21, 2021, and from the Chinese patent application 202011195096.3 filed Oct. 30, 2020, the content of which are incorporated herein in the entirety by reference.

TECHNICAL FIELD

The present disclosure relates to the technical field of artificial joint, in particular to the hip prosthesis containing zirconium-niobium alloy on oxidation layer and its preparation method.

BACKGROUND TECHNOLOGY

Total hip arthroplasty is one of the most important and effective procedures for the treatment of femoral head necrosis, hip dysplasia, degenerative hip osteoarthritis, rheumatoid arthritis and other end stage diseases. With the aging of the population, the number of patients with this type of surgery is increasing year by year.

Currently, the artificial hip prostheses used in clinical practice include bone cement fixation prosthesis and cementless fixation prosthesis. Among them, cementless prosthesis has been more and more widely used because of its good bone ingrown performance.

The bone integration interface of cementless fixed hip prosthesis usually adopts the following two approaches: one is to spray hydroxyapatite or titanium coating on stem surface, and the other is cones with trabecular porous structure printed on the surface, and stem and cones will be assembled afterward. But the surface coating in the first way has the risk of falling off, which affects the use effect. In the second approach, cones are an assembly structure with stem. Clinical studies show that, in order to combine cones with stem in structural design, there is a problem of sudden cross section change in the head and neck of bone handle in structural design, which is very serious stress concentration at these positions. Clinically, the main risks faced by fit handle include serious stress concentration in head and neck of bone handle, and risk of failure of fit between fit and cones. These risks may result in the failure of the entire hip prosthesis system.

In terms of the design and application of trabecular shell, the uniform trabecular design method is adopted in the trabecular shell manufactured by many domestic medical device companies. However, the uneven pressure distribution between shell and pelvis leads to uneven pressure and strain distribution in pelvis. The main problem is that only a few areas of the pelvis near the top of shell meet the conditions for bone growth, and most bone tissues in contact with shell do not meet the conditions for bone growth, which is easy to cause bone nongrowth or osteolysis due to excessive or too small compressive strain in clinical practice.

At present, the trabecular structure on the outer surface of femoral stem is mostly uniformly distributed. Clinical data show that the femoral stem and bone tissue with uniform trabecular structure are not ideal for bone growth in the upper lateral, lower medial and lower lateral of the femoral stem. Further studies show that the main reason for the unsatisfactory bone growth in the upper lateral and lower medial regions is that the contact pressure between femoral stem and bone tissue is small, and the compressive strain value of bone tissue combined with the upper lateral and lower medial regions of femoral stem is relatively small, e.g. less than 1000 microstrains, which does not meet the growth conditions of bone tissue. Meanwhile, in the lower lateral region, the contact pressure between femoral stem and bone tissue is too large, and the compressive strain value of bone tissue combined with femoral stem is too large, higher than 3000 microstrain, which does not meet the growth conditions of bone tissue. Therefore, uniform trabecular can overcome the problems of coating handle falling off and combination handle cone connection failure, but uniform growth of bone tissue on trabecular structure cannot be guaranteed.

In terms of the preparation of femoral head and liners, the existing methods of assembling femoral head and liners mainly include titanium alloy head, high crosslinked polyethylene, ceramic head and ceramic lined. However, the assembly of titanium alloy heads and high crosslinked polyethylene liners has a problem of the debris formed by the wear of high crosslinked polyethylene is prone to osteolysis. In addition, ceramic head and ceramic-lined shock resistance is relatively poor, which will cause the failure of the prosthesis due to impact.

Zirconium-niobium alloy has been gradually used in the field of medical devices for its excellent corrosion resistance, mechanical properties and good biocompatibility. Zirconium-niobium alloy can react with N, C, O or other elements to form a hard oxidation layer on the surface. It has excellent wear resistance and low wear rate, which can reduce the wear of soft materials, that is, it has excellent wear resistance of joint articular surface. Moreover, the ceramic layer can reduce the release of metal ions and has excellent biocompatibility, that is, excellent biocompatibility at the osseointegration interface. The low wear rate of the articular surface is combined organically with the osseointegration interface (trabeculae), which has excellent bone ingrowth performance, enabling the prosthesis to achieve the advantages of both interfaces at the same time.

3D printing technology, as an additive manufacturing technology, breaks through the manufacturing process-oriented product design concepts, and realizes the performance-oriented product design concept, that is, to solve the problem of complex parts that are difficult to form as a whole, and to reduce the waste of raw materials and energy caused by machining and manufacturing. However, the 3D printing products are prone to problems such as uneven microstructure and internal defects, and poor mechanical properties. The failure of powder fusion in part of trabecular structure also results in poor mechanical properties. Therefore, it is of great significance to fabricate a hip prosthesis containing zirconium-niobium alloy on oxidation layer with excellent mechanical properties and realize the advantages of two interfaces.

SUMMARY OF THE DISCLOSURE

One of the objectives of the present disclosure is to overcome the deficiencies of the existing technology to provide a hip prosthesis containing zirconium-niobium alloy on oxidation layer.

The second purpose of the present disclosure is to provide a preparation method of the hip prosthesis containing zirconium-niobium alloy on oxidation layer.

The technical scheme of the present disclosure is outlined as follows:

The preparation method of the hip prosthesis containing zirconium-niobium alloy on oxidation layer includes the following steps:

1) Preparation of Shell and Femoral Stem:
   1-1) Using zirconium-niobium alloy powder as the raw material, conducting a 3D printing for one-piece molding, and obtaining a first intermediate of shell and a first intermediate of femoral stem respectively, putting the two first intermediates into the Sinter-hip furnace, heating to 1250° C.-1400° C. under helium/argon gas protection, placing at a constant pressure of 140 MPa-180 MPa for 1 h to 3 h, reducing to a normal pressure, cooling to below 200° C. with the furnace, taking them out, and obtaining a second intermediate of shell and a second intermediate of femoral stem;
   1-2) Placing two second intermediate products in a programmable cooling box to cool to −80° C. to −120° C. at a rate of 1° C./min, keeping them at a constant temperature for 5 h to 10 h, and taking them out of the programmable cooling box; placing them in a liquid nitrogen for 16 h to 36 h, and adjusting the temperature to a room temperature so as to obtain a third intermediate of shell and a third intermediate of femoral stem;
   1-3) Placing two third intermediate products in a programmable cooling box to cool to −80° C. to −120° C. at a rate of 1° C./min, and placing them at a constant temperature for 5 h to 10 h, taking them out of the programmable cooling box, placing them in the liquid nitrogen for 16 h to 36 h and adjusting the temperature to room temperature so as to obtain a fourth intermediate of shell and a fourth intermediate of femoral stem;
   1-4) Machining, finishing, polishing, cleaning, and drying the fourth intermediate products, and obtaining a fifth intermediate of shell and a fifth intermediate of femoral stem;
   1-5) Placing the two fifth intermediate products in a tube furnace, introducing normal-pressure helium/argon gas containing 5% to 15% of oxygen in percentage by mass, heating to 500° C. to 700° C. at 5° C./min to 20° C./min, and cooling down to 400° C. to 495° C. at 0.4° C./min to 0.9° C./min; and cooling to be below 200° C. sequentially, taking them out to obtain the shell and femoral stem.
2) Preparation of Liners and Femoral Head:
   2-1) Machining, finishing, polishing, cleaning, and drying forged pieces containing zirconium-niobium alloy to obtain the intermediate products of liners or femoral head; the roughness of the inner and outer surfaces of the intermediate products of liners is Ra≤0.050 μm; the outer surface roughness of the intermediate products of femoral head is Ra≤0.050 μm;
   2-2) placing the intermediate products of liners and femoral head in a tube furnace, introducing normal-pressure helium/argon gas containing 5% to 15% of oxygen in percentage by mass, heating to 500° C. to 700° C. at 5° C./min to 20° C./min, and cooling to 400° C. to 495° C. at 0.4° C./min to 0.9° C./min; and natural cooling to be below 200° C. sequentially, taking them out to obtain the liners and femoral head.

The structure of the shell is the same as its first intermediate, second intermediate, third intermediate, fourth intermediate and fifth intermediate.

The structure of the femoral stem is the same as its first intermediate, second intermediate, third intermediate, fourth intermediate, and fifth intermediate.

The hip prosthesis containing zirconium-niobium alloy on oxidation layer comprises a femoral stem 1, a femoral head 2, liners 3 and a shell 4.

The femoral stem comprises a cylindrical head 11, a neck 12 and a hilt 13; the hilt 13 comprises a proximal hilt 14 and a distal hilt 15; a stem trabeculae 16 is arranged on the outer surface of the proximal hilt 14, the stem trabeculae 16 is partitioned into a lateral upper zone 1101, a lateral lower zone 1102, a medial upper zone 191 and a medial lower zone 192; the trabeculae arranged in the lateral upper zone 1101 and medial lower zone 192 are a first trabeculae 112; a trabeculae arranged in the medial upper zone 191 is a second trabeculae 113; a trabeculae arranged in the lateral lower zone 1102 is a third trabeculae 114; the pore size and porosity of the first trabeculae 112 are sequentially smaller than that of the second trabeculae 113 and the third trabeculae 114.

The shell comprises a hemispherical body 49, the middle part of which is provided with a first circular hole 41 with internal thread, and the outer surface of the hemispherical body is provided with a shell trabeculae 43, which is partitioned setting; a first partition line 46 intersects with a second partition line 45; the intersection point crosses the center of the first circular hole 41, and a third partition line 44 has circular shape and is located near the edge of the hemispherical body 49; the first, second and third partition lines divide the outer surface of the hemispherical body into a first upper region 471, a first lower region 472, a second upper region 473, a second lower region 474, a third upper region 475, a third lower region 476, a fourth upper region 477 and a fourth lower region 478; the area of the first upper region, the second upper region, the third upper region and the fourth upper region is equal; 3 second round holes 42 with internal thread are arranged on one side of the hemispherical body, two of which are respectively arranged in the first upper region 471 and the third upper region 475, and another is arranged in the junction of the first upper region 471 and the third upper region 475.

A fourth trabeculae 481 is arranged on the third upper region and fourth upper region respectively, a fifth trabeculae 482 is arranged on the third lower region and fourth lower region respectively, a sixth trabeculae 483 is arranged on the first upper region, a seventh trabeculae 484 is arranged on the first lower region, an eighth trabeculae 485 is arranged on the second upper region, and a ninth trabeculae 486 is arranged on the second lower region; the pore size and porosity of the fourth trabeculae are sequentially smaller than that of the fifth trabeculae, the sixth trabeculae, the seventh trabeculae, the eighth and the ninth trabeculae.

The chemical composition of the zirconium-niobium alloy powder in percentage by mass is respectively 85.6%-96.5% of Zr, 1.0%-12.5% of Nb, and the rest are unavoidable impurities; where a particle size of the zirconium-niobium alloy powder ranges from 45 to 150 μm.

The chemical composition of the forged pieces of zirconium-niobium alloy in percentage by mass includes 85.6%-96.5% of Zr and 1.0%-12.5% of Nb, and the residual is unavoidable impurities.

The specific steps for adjusting the temperature in steps 1-2) and 1-3) are: increasing the temperature to −120° C. to −80° C. and keeping the constant temperature for 3 h to 5 h; then increasing the temperature to −40° C. to −20° C. and keeping the constant temperature for 3 h to 5 h and then increasing the temperature to 4° C. to 8° C. and keeping the constant temperature for 1 h to 3 h and then increasing the temperature.

The pore size of the first trabeculae 112 ranges from 700 μm to 770 μm, and the porosity ranges from 65% to 75%; the second trabeculae 113 has pore size ranging from 780 μm to 850 μm and porosity ranging from 76% to 80%. The third trabeculae 114 has pore size ranging from 860 μm to 950 μm and porosity ranging from 81% to 85%. The thickness of the first trabeculae, the second trabeculae and the third trabeculae are equal to 1.2 mm to 1.5 mm.

The fourth trabeculae 481 has pore size ranging from 700 μm to 740 μm and porosity ranging from 65% to 70%; the fifth trabeculae 482 has pore size of 750 μm to 770 μm and porosity ranging from 71% to 75%; the sixth trabeculae 483 has pore size ranging from 780 μm to 810 μm and porosity ranging from 76% to 78%; the seventh trabeculae 484 has pore size ranging from 820 μm to 850 μm and porosity ranging from 79% to 80%. The eighth trabeculae 485 has pore size ranging from 860 μm to 900 μm and porosity ranging from 81% to 83%; the ninth trabeculae 486 has pore size of 910 μm to 950 μm and a porosity of 84% to 85%; the fourth trabeculae, fifth trabeculae, sixth trabeculae, seventh trabeculae, eighth trabeculae and ninth trabeculae have the same thickness of 1.2 mm to 1.5 mm.

The hip prosthesis containing zirconium-niobium alloy on oxidation layer prepared by the above method.

Compared with the existing technical solutions, the present disclosure has the following beneficial effects:

The femoral stem and shell of the hip prosthesis containing zirconium-niobium alloy on oxidation layer of the present disclosure are integrated with 3D printing, which solves the problem that the complex structure cannot be prepared by traditional machining and cones and stem handle body fail to match; and has high bonding strength between trabeculae and the matrix, therefore it is not easy to fall off, thereby improving the service life of the prosthesis.

The femoral stem prepared by the present disclosure solves the problem of bone absorption caused by too small or too large compressive strain value of femur in the lateral and medial lower regions of uniform trabeculae, so that most of the compressive strain values of the femoral bone tissue are in the range of 1000-3000 microstrains, which conforms to the bone growth theory and ensures the uniform growth of bone in the trabecular region.

The shell prepared by the present disclosure adopts partitioned trabeculae to provide a suitable environment for bone growth. According to the results of finite element analysis, the area in bone tissue finite element model that meets the conditions of bone growth can reach 40%, realizing bone integration between shell and host bone.

The integral hip prosthesis containing zirconium-niobium alloy on oxidation layer of the present disclosure realizes the excellent biocompatibility of bone integration interface, bone ingrowth ability, super wear resistance and low wear rate of friction interface. The femoral head and liners are oxidized to form a ceramic surface to achieve ultra-high wear resistance and low wear rate of the friction interface. Femoral stem and shell achieve excellent bone ingrowth and biocompatibility of bone integration interface.

The hip prosthesis according to the present disclosure has low artifact, little interference to nuclear magnetic field and can be used for nuclear magnetic detection.

DETAILED DESCRIPTION OF THE EMBODIMENTS

Figure 1:
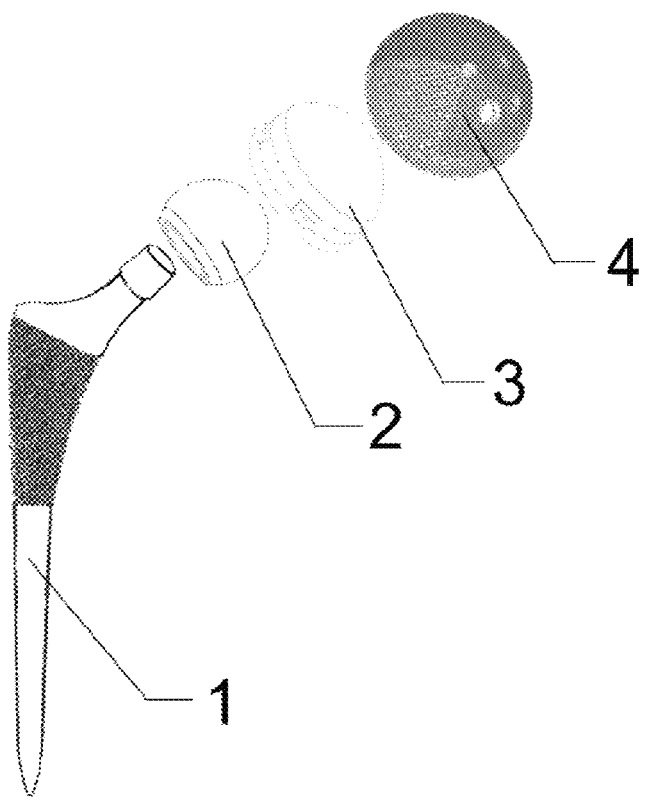
FIG. 1 is a schematic diagram of hip prosthesis containing zirconium-niobium alloy on oxidation layer of the present disclosure.

The present disclosure will be further described below with the drawings and embodiments.

Embodiment 1

The preparation method of the hip prosthesis containing zirconium-niobium alloy on oxidation layer includes the following steps:

1) Preparation of Shell and Femoral Stem:
   1-1) Using zirconium-niobium alloy powder as the raw material, conducting a 3D printing for one-piece molding, and obtaining a first intermediate of shell and a first intermediate of femoral stem respectively, putting the two first intermediates into the Sinter-hip furnace, heating to 1250° C. under helium gas protection, placing at a constant pressure of 180 MPa for 3 h, reducing to a normal pressure, cooling to below 200° C. with the furnace, taking them out, and obtaining a second intermediate of shell and a second intermediate of femoral stem;
   1-2) Placing two second intermediate products in a programmable cooling box to cool to −80° cat a rate of 1° C./min, keeping them at a constant temperature for 10 h, and taking them out of the programmable cooling box; placing them in a liquid nitrogen for 16 h, and adjusting the temperature to a room temperature so as to obtain a third intermediate of shell and a third intermediate of femoral stem;
   1-3) Placing two third intermediate products in a programmable cooling box to cool to −80° cat a rate of 1°

C./min, and placing them at a constant temperature for 10 h, taking them out of the programmable cooling box, placing them in the liquid nitrogen for 16 h and adjusting the temperature to room temperature so as to obtain a fourth intermediate of shell and a fourth intermediate of femoral stem;

1-4) Machining, finishing, polishing, cleaning, and drying the fourth intermediate products, and obtaining a fifth intermediate of shell and a fifth intermediate of femoral stem;

1-5) Placing the two fifth intermediate products in a tube furnace, introducing normal-pressure helium gas containing 5% of oxygen in percentage by mass, heating to 500° cat 5° C./min, and cooling down to 400° C. at 0.4° C./min; and cooling to be below 200° C. sequentially, taking them out to obtain the shell and femoral stem.

2) Preparation of Liners and Femoral Head:

2-1) Machining, finishing, polishing, cleaning, and drying forged pieces containing zirconium-niobium alloy to obtain the intermediate products of liners or femoral head; the roughness of the inner and outer surfaces of the intermediate products of liners is Ra=0.012 μm; the outer surface roughness of the intermediate products of femoral head is Ra=0.012 μm;

2-2) Placing the intermediate products of liners and femoral head in a tube furnace, introducing normal-pressure helium gas containing 5% to 15% of oxygen in percentage by mass, heating to 500° cat 5° C./min, and cooling to 400° cat 0.4° C./min; and natural cooling to be below 200° C. sequentially, taking them out to obtain the liners and femoral head.

The structure of the shell is the same as its first intermediate, second intermediate, third intermediate, fourth intermediate and fifth intermediate.

The structure of the femoral stem is the same as its first intermediate, second intermediate, third intermediate, fourth intermediate, and fifth intermediate.

Figure 9:
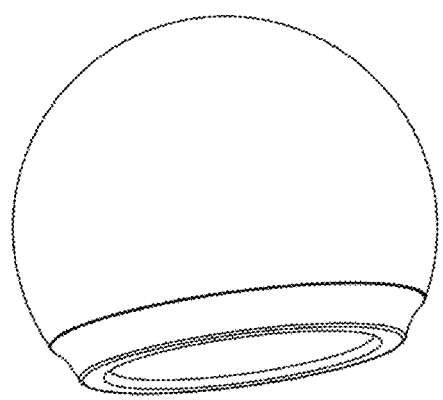
FIG. 9 is a schematic diagram of the femoral head.
Figure 10:
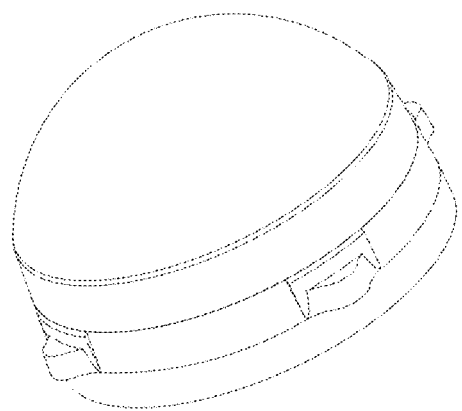
FIG. 10 is a schematic diagram of the liners.

As shown in FIG. 1, the hip prosthesis containing zirconium-niobium alloy on oxidation layer comprises a femoral stem 1, a femoral head 2 (as shown in FIG. 9), liners 3 (as shown in FIG. 10) and a shell 4.

Figure 2:
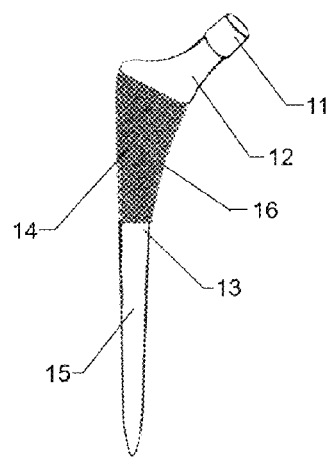
FIG. 2 is a schematic diagram of femoral stem.
Figure 3:
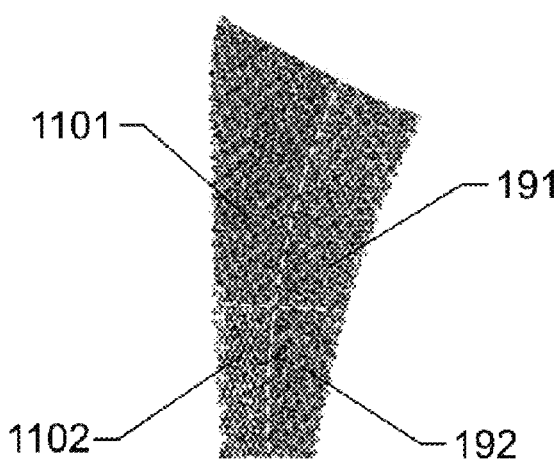
FIG. 3 shows the proximal partition of the femoral stem.
Figure 4:
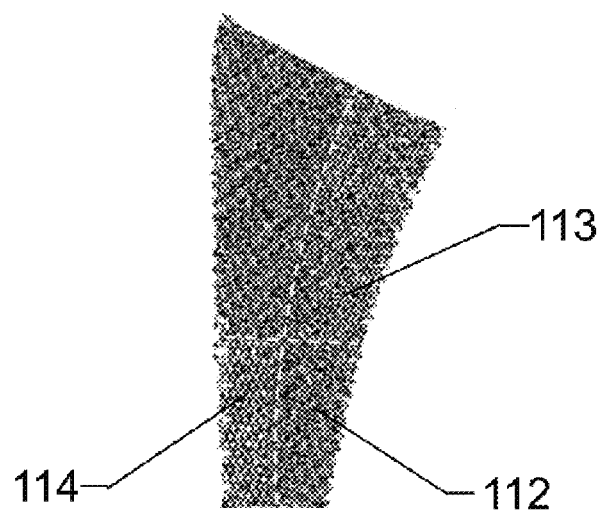
FIG. 4 shows the proximal structure of the femoral stem.
Figure 5:
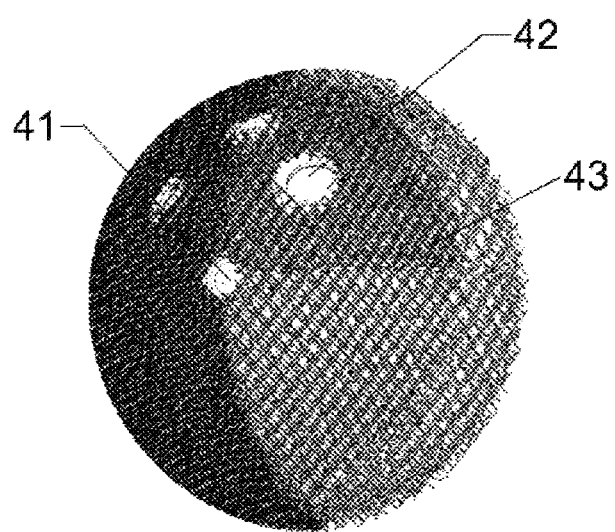
FIG. 5 is the axonometric diagram of the shell.
Figure 6:
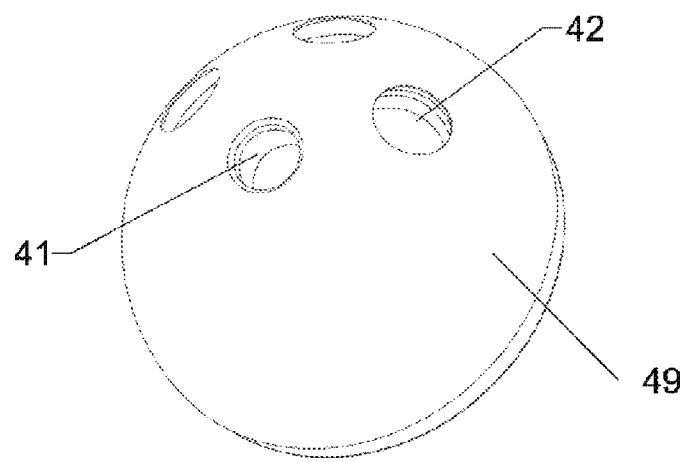
FIG. 6 is an axonometric diagram of shell (without trabeculae).
Figure 7:
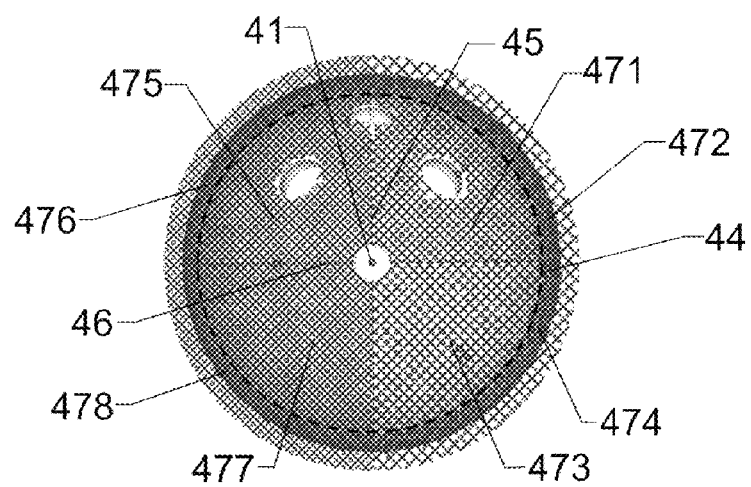
FIG. 7 is a schematic diagram of the shell structure.
Figure 8:
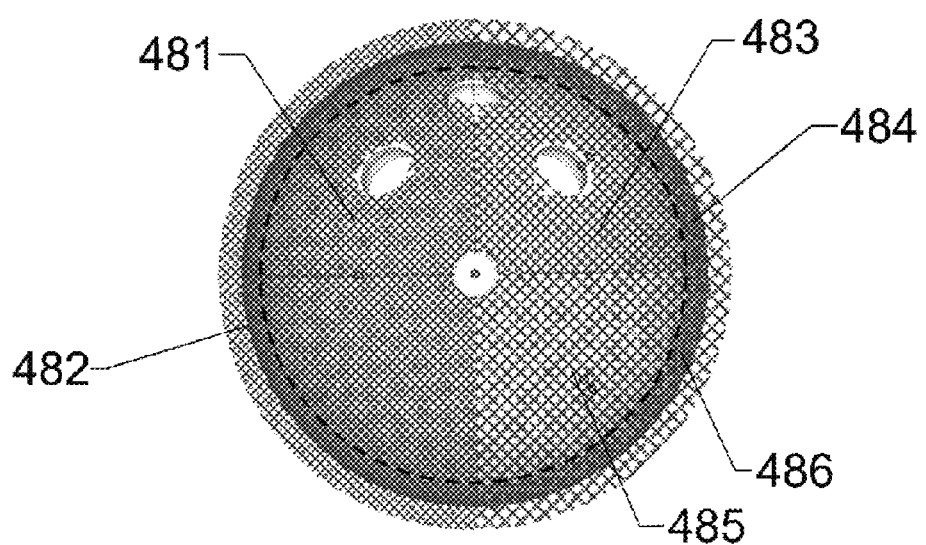
FIG. 8 is the top view of the shell.

As shown in FIG. 2-4, the femoral stem comprises a cylindrical head 11, a neck 12 and a hilt 13; the hilt 13 comprises a proximal hilt 14 and a distal hilt 15; a stem trabeculae 16 is arranged on the outer surface of the proximal hilt 14, the stem trabeculae 16 is partitioned into a lateral upper zone 1101, a lateral lower zone 1102, a medial upper zone 191 and a medial lower zone 192; the trabeculae arranged in the lateral upper zone 1101 and medial lower zone 192 are a first trabeculae 112; a trabeculae arranged in the medial upper zone 191 is a second trabeculae 113; a trabeculae arranged in the lateral lower zone 1102 is a third trabeculae 114.

As shown in FIGS. 5-8, the shell comprises a hemispherical body 49, the middle part of which is provided with a first circular hole 41 with internal thread, and the outer surface of the hemispherical body is provided with a shell trabeculae 43, which is partitioned setting; a first partition line 46 intersects with a second partition line 45; the intersection point crosses the center of the first circular hole 41, and a third partition line 44 has circular shape and is located near the edge of the hemispherical body 49; the first, second and third partition lines divide the outer surface of the hemispherical body into a first upper region 471, a first lower region 472, a second upper region 473, a second lower region 474, a third upper region 475, a third lower region 476, a fourth upper region 477 and a fourth lower region 478; the area of the first upper region, the second upper region, the third upper region and the fourth upper region is equal; 3 second round holes 42 with internal thread are arranged on one side of the hemispherical body 49, two of which are respectively arranged in the first upper region 471 and the third upper region 475, and another is arranged in the junction of the first upper region 471 and the third upper region 475.

A fourth trabeculae 481 is arranged on the third upper region and fourth upper region respectively, a fifth trabeculae 482 is arranged on the third lower region and fourth lower region respectively, a sixth trabeculae 483 is arranged on the first upper region, a seventh trabeculae 484 is arranged on the first lower region, an eighth trabeculae 485 is arranged on the second upper region, and a ninth trabeculae 486 is arranged on the second lower region.

The chemical composition of the zirconium-niobium alloy powder in percentage by mass is respectively 85.6% of Zr, 12.5% of Nb, and the rest are unavoidable impurities; where a particle size of the zirconium-niobium alloy powder ranges from 45 to 150 μm.

The chemical composition of the forged pieces of zirconium-niobium alloy in percentage by mass includes 85.6% of Zr and 12.5% of Nb, and the residual is unavoidable impurities.

The specific steps for adjusting the temperature in steps 1-2) and 1-3) are: increasing the temperature to −120° C. and keeping the constant temperature for 5 h; then increasing the temperature to −40° C. and keeping the constant temperature for 5 h and then increasing the temperature to 4° C. and keeping the constant temperature for 3 h and then increasing the temperature.

The pore size of the first trabeculae 112 is 700 μm, and the porosity is 65%; the second trabeculae 113 has pore size of 780 μm and porosity of 76%. The third trabeculae 114 has pore size of 860 μm and porosity of 81%; the thickness of the first trabeculae, the second trabeculae and the third trabeculae are equal to 1.2 mm.

The fourth trabeculae 481 has pore size of 700 μm and porosity of 65%; the fifth trabeculae 482 has pore size of 750 μm and porosity of 71%; the sixth trabeculae 483 has pore size of 780 μm and porosity of 76%; the seventh trabeculae 484 has pore size of 820 μm and porosity of 79%; the eighth trabeculae 485 has pore size of 860 μm and porosity of 81%; the ninth trabeculae 486 has pore size of 910 μm and a porosity of 84%; the fourth trabeculae, fifth trabeculae, sixth trabeculae, seventh trabeculae, eighth trabeculae and ninth trabeculae have the same thickness of 1.2 mm.

Embodiment 2

The preparation method of the hip prosthesis containing zirconium-niobium alloy on oxidation layer includes the following steps:

1) Preparation of Shell and Femoral Stem:

1-1) Using zirconium-niobium alloy powder as the raw material, conducting a 3D printing for one-piece molding, and obtaining a first intermediate of shell and a first intermediate of femoral stem respectively, putting the two first intermediates into the Sinter-hip furnace, heating to 1325° C. under argon gas protection, placing at a constant pressure of 160 MPa for 2 h, reducing to a normal pressure, cooling to below 200° C. with the furnace, taking them out, and obtaining a second intermediate of shell and a second intermediate of femoral stem;

1-2) Placing two second intermediate products in a programmable cooling box to cool to −100° C at a rate of 1° C./min, keeping them at a constant temperature for 7 h, and taking them out of the programmable cooling box; placing them in a liquid nitrogen for 24 h, and adjusting the temperature to a room temperature so as to obtain a third intermediate of shell and a third intermediate of femoral stem;

1-3) Placing two third intermediate products in a programmable cooling box to cool to −100° C at a rate of 1° C./min, and placing them at a constant temperature for 7 h, taking them out of the programmable cooling box, placing them in the liquid nitrogen for 24 h and adjusting the temperature to room temperature so as to obtain a fourth intermediate of shell and a fourth intermediate of femoral stem;

1-4) Machining, finishing, polishing, cleaning, and drying the fourth intermediate products, and obtaining a fifth intermediate of shell and a fifth intermediate of femoral stem;

1-5) Placing the two fifth intermediate products in a tube furnace, introducing normal-pressure argon gas containing 10% of oxygen in percentage by mass, heating to 600° C at 15° C./min, and cooling down to 450° C at 0.7° C./min; and cooling to be below 200° C. sequentially, taking them out to obtain the shell and femoral stem.

2) Preparation of Liners and Femoral Head:

2-1) Machining, finishing, polishing, cleaning, and drying forged pieces containing zirconium-niobium alloy to obtain the intermediate products of liners or femoral head; the roughness of the inner and outer surfaces of the intermediate products of liners is Ra=0.035 µm; the outer surface roughness of the intermediate products of femoral head is Ra=0.035 µm;

2-2) Placing the intermediate products of liners and femoral head in a tube furnace, introducing normal-pressure argon gas containing 10% of oxygen in percentage by mass, heating to 600° C at 15° C./min, and cooling to 450° C at 0.7° C./min; and natural cooling to be below 200° C. sequentially, taking them out to obtain the liners and femoral head.

The structure of the shell is the same as its first intermediate, second intermediate, third intermediate, fourth intermediate and fifth intermediate.

The structure of the femoral stem is the same as its first intermediate, second intermediate, third intermediate, fourth intermediate, and fifth intermediate.

The hip prosthesis containing zirconium-niobium alloy on oxidation layer comprises a femoral stem 1, a femoral head 2, liners 3 and a shell 4.

The femoral stem comprises a cylindrical head 11, a neck 12 and a hilt 13; the hilt 13 comprises a proximal hilt 14 and a distal hilt 15; a stem trabeculae 16 is arranged on the outer surface of the proximal hilt 14, the stem trabeculae 16 is partitioned into a lateral upper zone 1101, a lateral lower zone 1102, a medial upper zone 191 and a medial lower zone 192; the trabeculae arranged in the lateral upper zone 1101 and medial lower zone 192 are a first trabeculae 112; a trabeculae arranged in the medial upper zone 191 is a second trabeculae 113; a trabeculae arranged in the lateral lower zone 1102 is a third trabeculae 114.

The shell comprises a hemispherical body 49, the middle part of which is provided with a first circular hole 41 with internal thread, and the outer surface of the hemispherical body is provided with a shell trabeculae 43, which is partitioned setting; a first partition line 46 intersects with a second partition line 45; the intersection point crosses the center of the first circular hole 41, and a third partition line 44 has circular shape and is located near the edge of the hemispherical body 49; the first, second and third partition lines divide the outer surface of the hemispherical body into a first upper region 471, a first lower region 472, a second upper region 473, a second lower region 474, a third upper region 475, a third lower region 476, a fourth upper region 477 and a fourth lower region 478; the area of the first upper region, the second upper region, the third upper region and the fourth upper region is equal; 3 second round holes 42 with internal thread are arranged on one side of the hemispherical body 49, two of which are respectively arranged in the first upper region 471 and the third upper region 475, and another is arranged in the junction of the first upper region 471 and the third upper region 475.

A fourth trabeculae 481 is arranged on the third upper region and fourth upper region respectively, a fifth trabeculae 482 is arranged on the third lower region and fourth lower region respectively, a sixth trabeculae 483 is arranged on the first upper region, a seventh trabeculae 484 is arranged on the first lower region, an eighth trabeculae 485 is arranged on the second upper region, and a ninth trabeculae 486 is arranged on the second lower region.

The chemical composition of the zirconium-niobium alloy powder in percentage by mass is respectively 93.4% of Zr, 5.1% of Nb, and the rest are unavoidable impurities; where a particle size of the zirconium-niobium alloy powder ranges from 45 to 150 µm.

The chemical composition of the forged pieces of zirconium-niobium alloy in percentage by mass includes 93.4% of Zr and 5.1% of Nb, and the residual is unavoidable impurities.

The specific steps for adjusting the temperature in steps 1-2) and 1-3) are: increasing the temperature to −100° C. and keeping the constant temperature for 4 h; then increasing the temperature to −30° C. and keeping the constant temperature for 4 h and then increasing the temperature to 6° C. and keeping the constant temperature for 2 h and then increasing the temperature.

The pore size of the first trabeculae 112 is 740 µm, and the porosity is 70%; the second trabeculae 113 has pore size of 810 µm and porosity of 78%. The third trabeculae 114 has pore size of 900 µm and porosity of 83%; the thickness of the first trabeculae, the second trabeculae and the third trabeculae are equal to 1.3 mm.

The fourth trabeculae 481 has pore size of 720 µm and porosity of 67%; the fifth trabeculae 482 has pore size of 760 µm and porosity of 73%; the sixth trabeculae 483 has pore size of 800 µm and porosity of 77%; the seventh trabeculae 484 has pore size of 840 µm and porosity of 79.5%; the eighth trabeculae 485 has pore size of 880 µm and porosity of 82%; the ninth trabeculae 486 has pore size of 930 µm and a porosity of 84.5%; the fourth trabeculae, fifth trabeculae, sixth trabeculae, seventh trabeculae, eighth trabeculae and ninth trabeculae have the same thickness of 1.3 mm.

Embodiment 3

The preparation method of the hip prosthesis containing zirconium-niobium alloy on oxidation layer includes the following steps:

1) Preparation of Shell and Femoral Stem:

1-1) Using zirconium-niobium alloy powder as the raw material, conducting a 3D printing for one-piece molding, and obtaining a first intermediate of shell and a first intermediate of femoral stem respectively, putting the two first intermediates into the Sinter-hip furnace, heating to 1400° C. under argon gas protection, placing at a constant pressure of 140 MPa for 1 h, reducing to a normal pressure, cooling to below 200° C. with the furnace, taking them out, and obtaining a second intermediate of shell and a second intermediate of femoral stem;

1-2) Placing two second intermediate products in a programmable cooling box to cool to −120° cat a rate of 1° C./min, keeping them at a constant temperature for 5 h, and taking them out of the programmable cooling box; placing them in a liquid nitrogen for 36 h, and adjusting the temperature to a room temperature so as to obtain a third intermediate of shell and a third intermediate of femoral stem;

1-3) Placing two third intermediate products in a programmable cooling box to cool to −120° C. at a rate of 1° C./min, and placing them at a constant temperature for 5 h, taking them out of the programmable cooling box, placing them in the liquid nitrogen for 36 h and adjusting the temperature to room temperature so as to obtain a fourth intermediate of the shell and a fourth intermediate of the femoral stem;

1-4) Machining, finishing, polishing, cleaning, and drying the fourth intermediate products, and obtaining a fifth intermediate of the shell and a fifth intermediate of the femoral stem;

1-5) Placing the two fifth intermediate products in a tube furnace, introducing normal-pressure argon gas containing 15% of oxygen in percentage by mass, heating to 700° cat 20° C./min, and cooling down to 495° cat 0.9° C./min; and cooling to be below 200° C. sequentially, taking them out to obtain the shell and femoral stem.

2) Preparation of Liners and Femoral Head:

2-1) Machining, finishing, polishing, cleaning, and drying forged pieces containing zirconium-niobium alloy to obtain the intermediate products of liners or femoral head; the roughness of the inner and outer surfaces of the intermediate products of liners is Ra=0.050 µm; the outer surface roughness of the intermediate products of femoral head is Ra=0.050 µm;

2-2) placing the intermediate products of liners and femoral head in a tube furnace, introducing normal-pressure argon gas containing 15% of oxygen in percentage by mass, heating to 700° C. at 20° C./min, and cooling to 495° cat 0.9° C./min; and natural cooling to be below 200° C. sequentially, taking them out to obtain the liners and femoral head.

The structure of the shell is the same as its first intermediate, second intermediate, third intermediate, fourth intermediate and fifth intermediate.

The structure of the femoral stem is the same as its first intermediate, second intermediate, third intermediate, fourth intermediate, and fifth intermediate.

The hip prosthesis containing zirconium-niobium alloy on oxidation layer comprises a femoral stem 1, a femoral head 2, liners 3 and a shell 4.

The femoral stem comprises a cylindrical head 11, a neck 12 and a hilt 13; the hilt 13 comprises a proximal hilt 14 and a distal hilt 15; a stem trabeculae 16 is arranged on the outer surface of the proximal hilt 14, the stem trabeculae 16 is partitioned into a lateral upper zone 1101, a lateral lower zone 1102, a medial upper zone 191 and a medial lower zone 192; the trabeculae arranged in the lateral upper zone 1101 and medial lower zone 192 are a first trabeculae 112; a trabeculae arranged in the medial upper zone 191 is a second trabeculae 113; a trabeculae arranged in the lateral lower zone 1102 is a third trabeculae 114.

The femoral shell comprises a hemispherical body 49, the middle part of which is provided with a first circular hole 41 with internal thread, and the outer surface of the hemispherical body is provided with a shell trabeculae 43, which is partitioned setting; a first partition line 46 intersects with a second partition line 45; the intersection point crosses the center of the first circular hole 41, and a third partition line 44 has circular shape and is located near the edge of the hemispherical body 49; the first, second and third partition lines divide the outer surface of the hemispherical body into a first upper region 471, a first lower region 472, a second upper region 473, a second lower region 474, a third upper region 475, a third lower region 476, a fourth upper region 477 and a fourth lower region 478; the area of the first upper region, the second upper region, the third upper region and the fourth upper region is equal; 3 second round holes 42 with internal thread are arranged on one side of the hemispherical body 49, two of which are respectively arranged in the first upper region 471 and the third upper region 475, and another is arranged in the junction of the first upper region 471 and the third upper region 475.

A fourth trabeculae 481 is arranged on the third upper region and fourth upper region respectively, a fifth trabeculae 482 is arranged on the third lower region and fourth lower region respectively, a sixth trabeculae 483 is arranged on the first upper region, a seventh trabeculae 484 is arranged on the first lower region, an eighth trabeculae 485 is arranged on the second upper region, and a ninth trabeculae 486 is arranged on the second lower region.

The chemical composition of the zirconium-niobium alloy powder in percentage by mass is respectively 96.5% of Zr, 1.0% of Nb, and the rest are unavoidable impurities; where a particle size of the zirconium-niobium alloy powder ranges from 45 to 150 µm.

The chemical composition of the forged pieces of zirconium-niobium alloy in percentage by mass includes 96.5% of Zr and 1.0% of Nb, and the residual is unavoidable impurities.

The specific steps for adjusting the temperature in steps 1-2) and 1-3) are: increasing the temperature to −80° C. and keeping the constant temperature for 3 h; then increasing the temperature to −20° C. and keeping the constant temperature for 3 h and then increasing the temperature to 8° C. and keeping the constant temperature for 1 h and then increasing the temperature.

The pore size of the first trabeculae 112 is 770 µm, and the porosity is 75%; the second trabeculae 113 has pore size of 850 µm and porosity of 80%. The third trabeculae 114 has pore size of 950 µm and porosity of 85%; the thickness of the first trabeculae, the second trabeculae and the third trabeculae are equal to 1.5 mm.

The fourth trabeculae 481 has pore size of 740 µm and porosity of 70%; the fifth trabeculae 482 has pore size of 770 µm and porosity of 75%; the sixth trabeculae 483 has pore size of 810 µm and porosity of 78%; the seventh trabeculae 484 has pore size of 850 µm and porosity of 80%; the eighth trabeculae 485 has pore size of 900 µm and porosity of 83%; the ninth trabeculae 486 has pore size of 950 µm and a porosity of 85%; the fourth trabeculae, fifth trabeculae, sixth trabeculae, seventh trabeculae, eighth trabeculae and ninth trabeculae have the same thickness of 1.5 mm.

Control Group 1

An uniform trabecular hip prosthesis system, the structure thereof is similar to that of the Embodiment 1, the different structure between the uniform trabecular hip prosthesis system and the Embodiment 1 are as follows:

a first trabeculae, a second trabeculae, and a third trabeculae of the femoral stem are the same trabeculae with a pore size of 780 μm, a porosity of 76%, and a trabecular thickness of 1.2 mm.

The fourth trabeculae, fifth trabeculae, sixth trabeculae, seventh trabeculae, eighth trabeculae and ninth trabeculae of the femoral shell are the same trabeculae with a pore size of 780 μm, a porosity of 76% and a trabecular thickness is 1.2 mm.

The others are the same as Embodiment 1.

The Control Group 2

Using the zirconium-niobium alloy powder (same as Embodiment 1) as raw material, femoral stem and shell with the same structure as Embodiment 1 can be obtained by conducting a 3D printing for one-piece molding.

Experiment Verification

Figure 11:
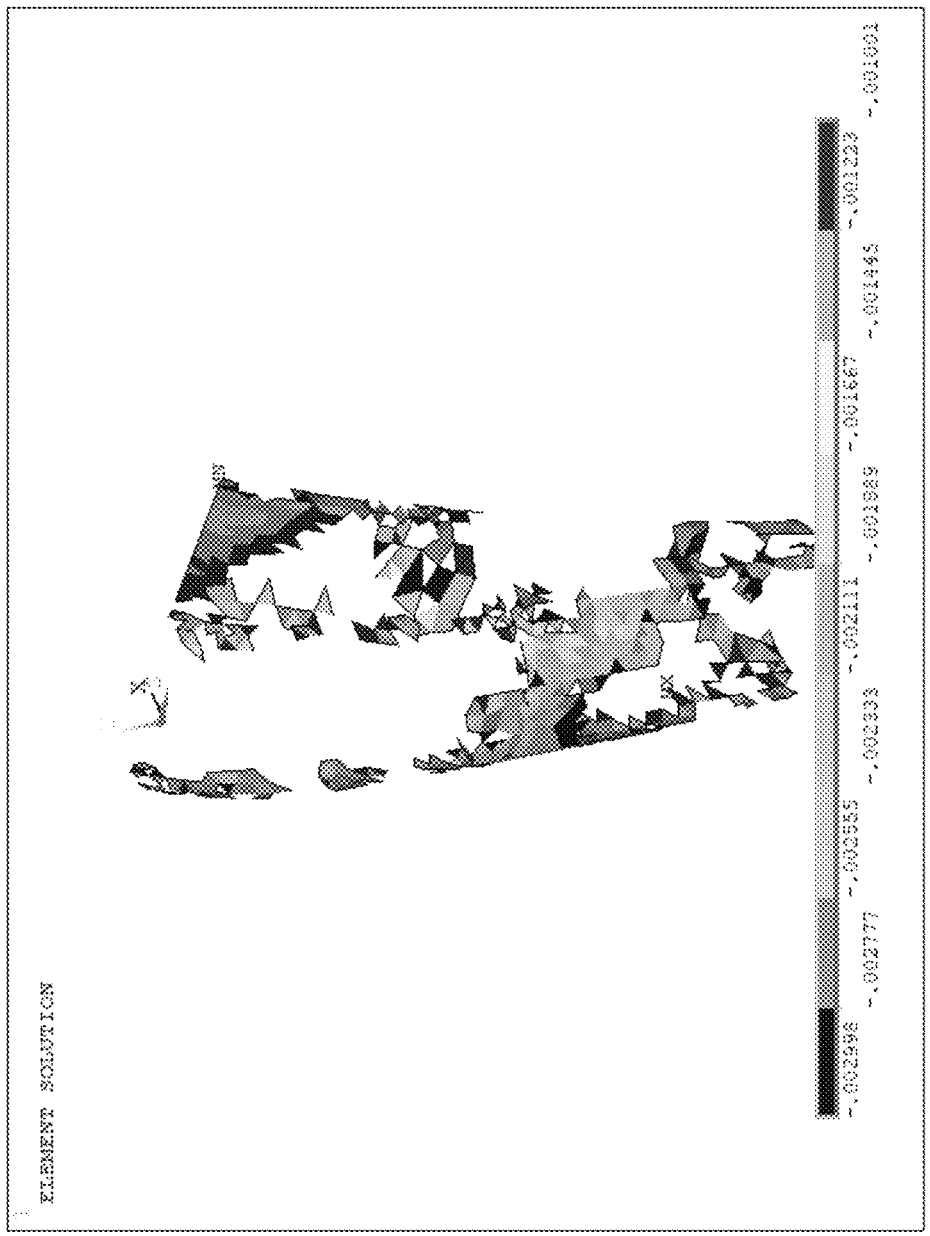
FIG. 11 is the cloud map of the femoral stem strain distribution in control group 1.
Figure 12:
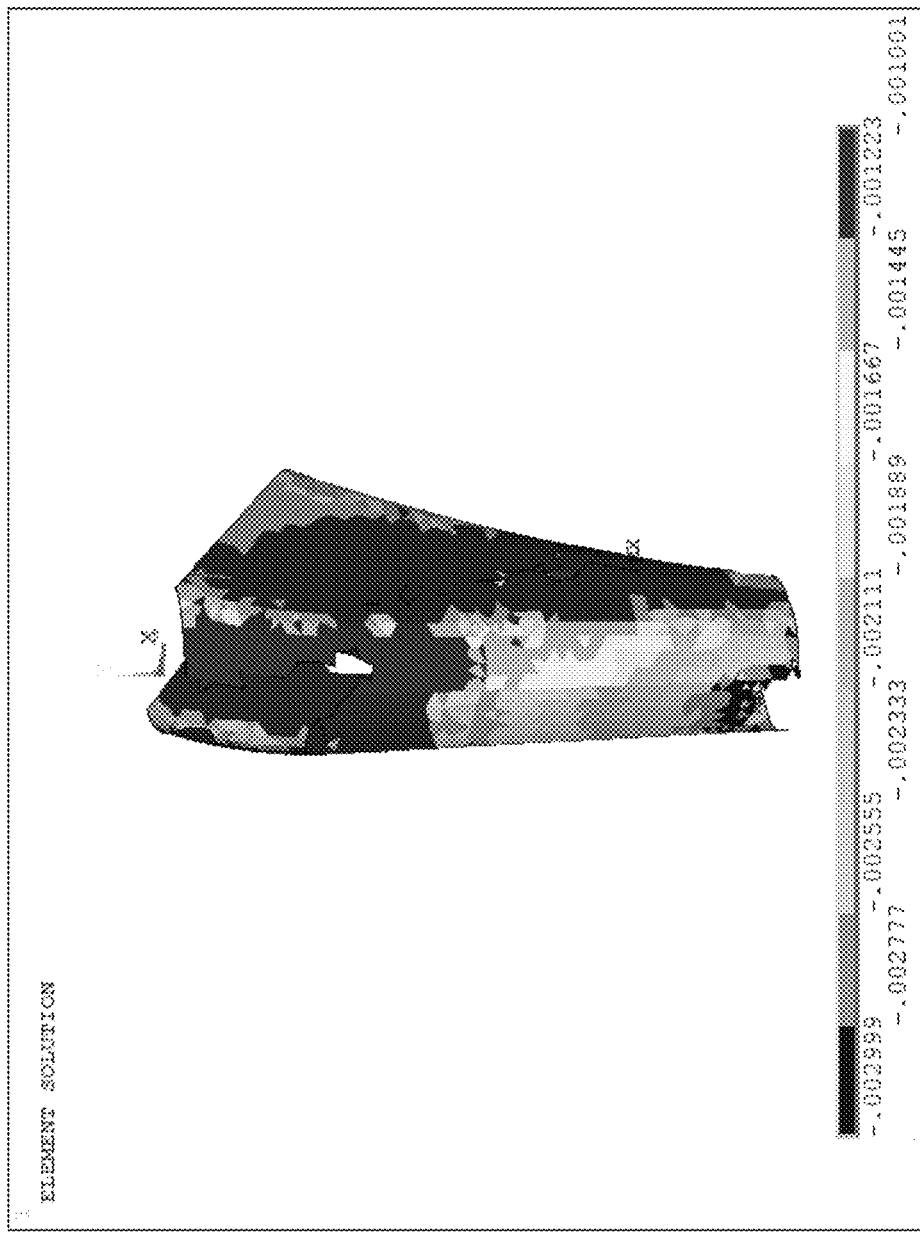
FIG. 12 is the femoral stem strain distribution cloud diagram of Embodiment 1.

The femoral stem finite element model of Embodiment 1 and the femoral stem finite element model of control group 1 were analyzed by finite element analysis method. The strain cloud map obtained by finite element analysis only showed the microstrain (shaded part) in the range of 1000-3000. As shown in FIG. 12, the 1000-3000 microstrain region of Embodiment 1 accounted for 75% of the entire bone tissue finite element model, which was larger than that in control group 1 (FIG. 11, 1000-3000 microstrain region accounted for 20%). It is suggested that the femoral stem of the hip prosthesis of the present disclosure is beneficial to bone ingrowth performance.

Figure 13:
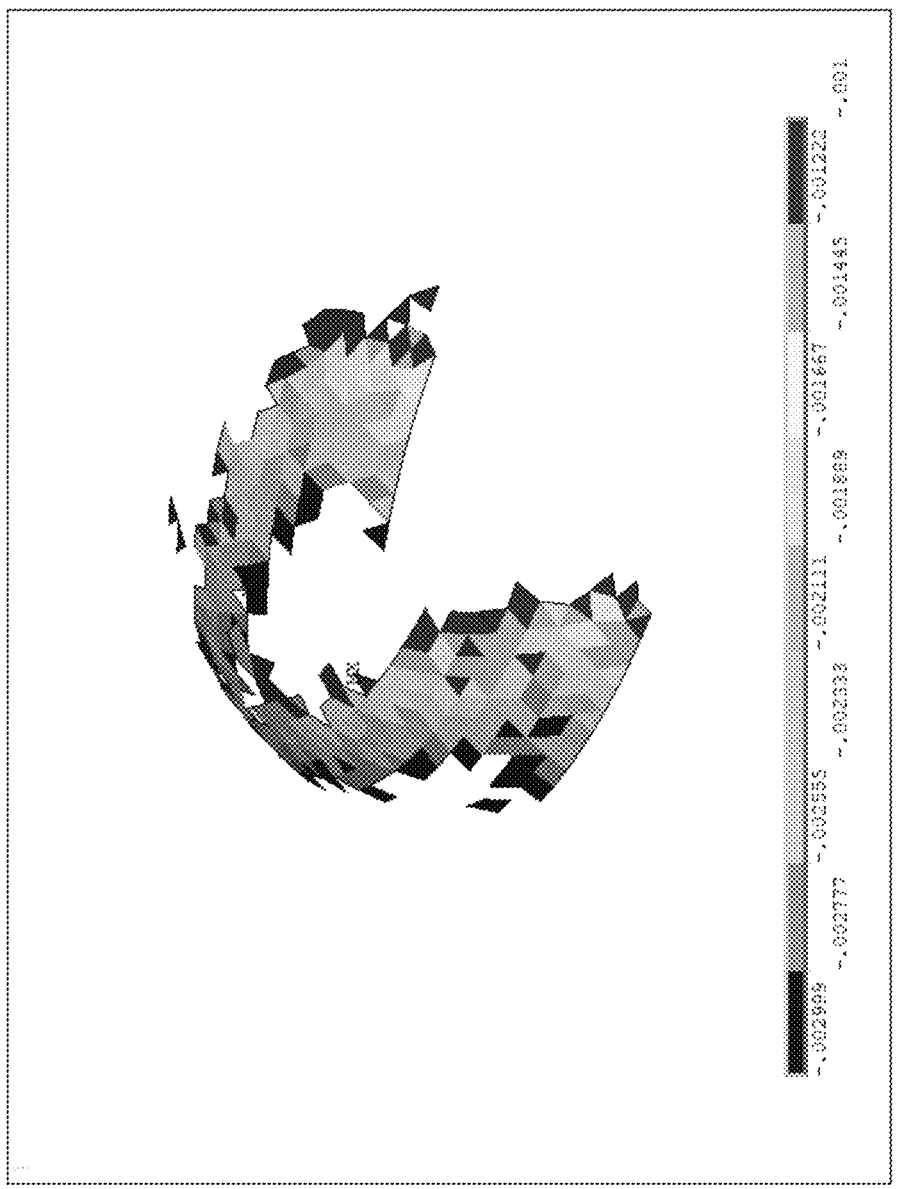
FIG. 13 is the cloud diagram of the shell strain distribution in control group 1.
Figure 14:
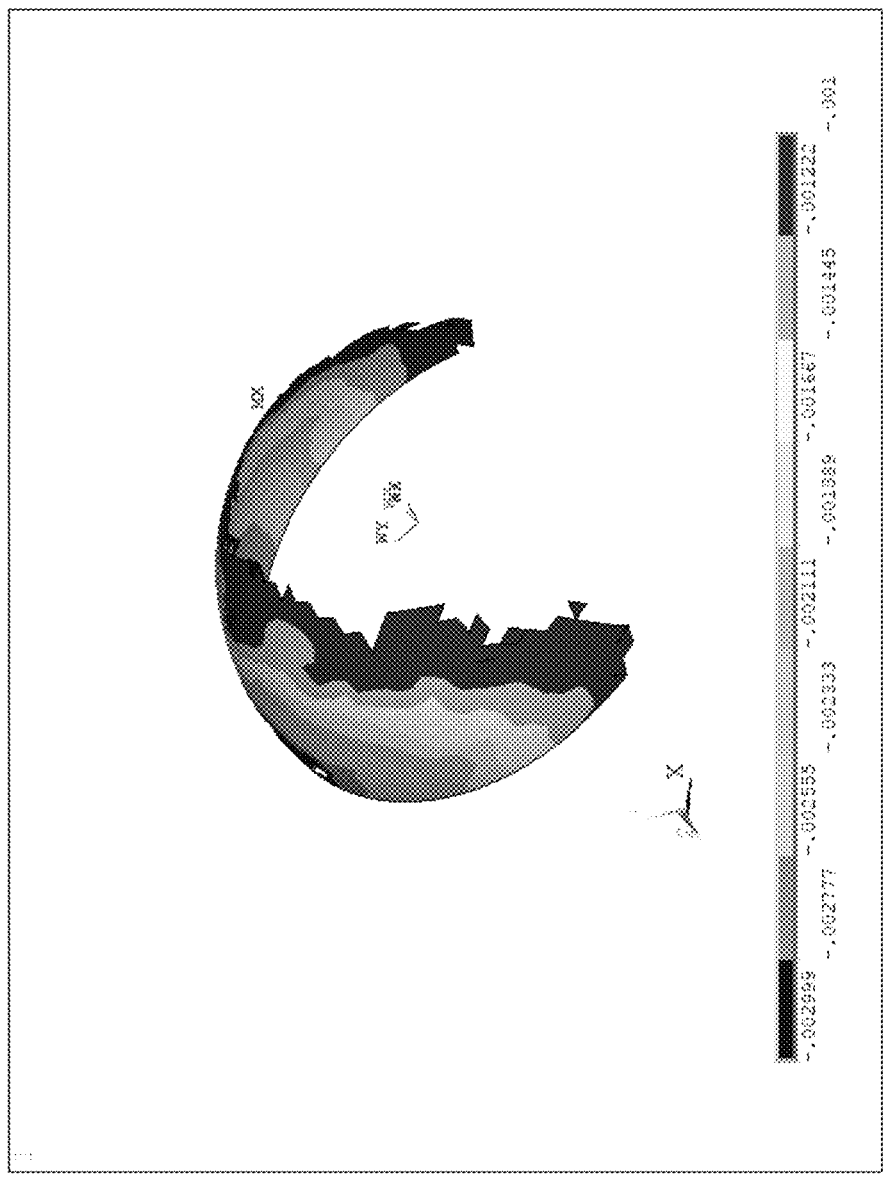
FIG. 14 shows the cloud diagram of the shell strain distribution in Embodiment 1.

The shell finite element model of Embodiment 1 and the shell finite element model of control group 1 were analyzed by finite element analysis method. The strain cloud map obtained by finite element analysis only showed the microstrain (shaded part) in the range of 1000-3000. As shown in FIG. 13, the 1000-3000 microstrain region of the shell of the Embodiment 1 accounted for 40% of the entire bone tissue finite element model, which was larger than that in control group 1 (FIG. 13, 1000-3000 microstrain region accounted for 15%). It is suggested that the femoral stem of the hip prosthesis of the present disclosure is beneficial to bone ingrowth performance.

The finite element analysis results show that the strain distribution cloud of the femoral stem in bone tissue finite element model of Embodiment 2 and 3 is similar to that of the femoral stem in bone tissue finite element model of Embodiment 1. The strain distribution cloud diagram of the shell in Embodiment 2 and 3 on bone tissue finite element model is similar to that of the shell in Embodiment 1 on bone tissue finite element model.

Figure 15:
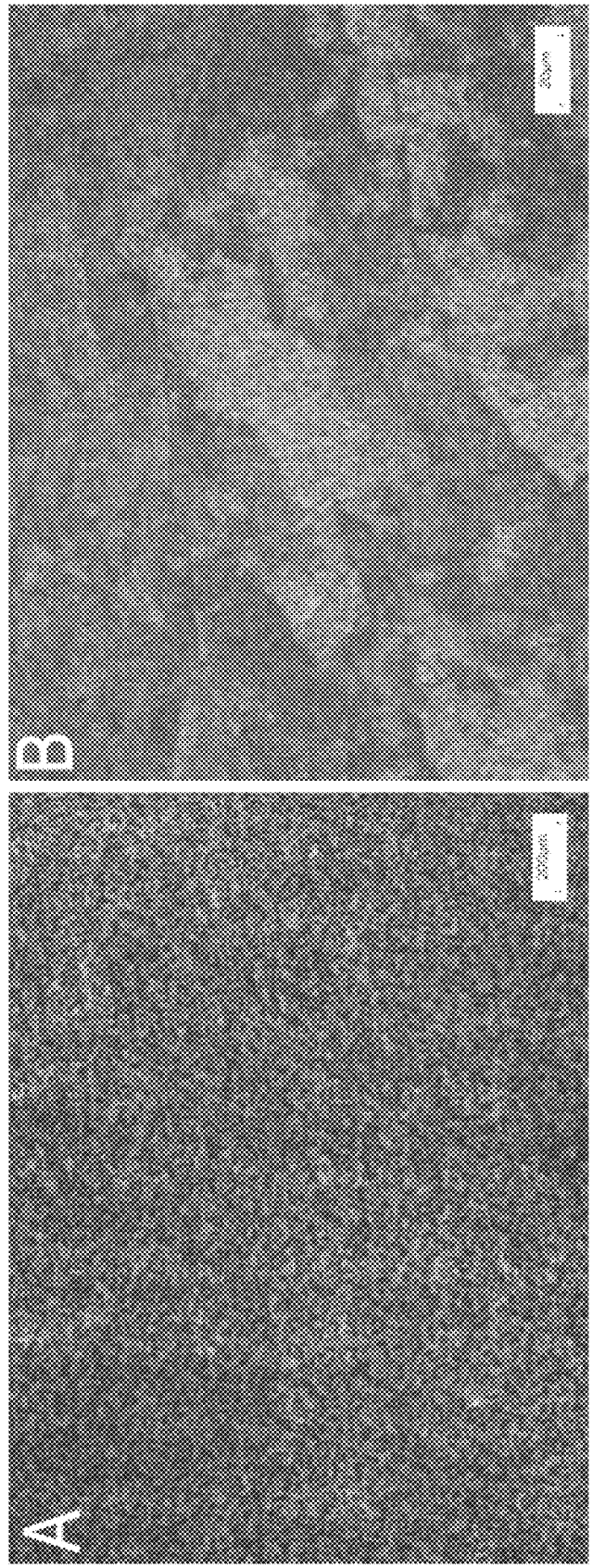
FIG. 15 shows the metallographic micro structure of femoral stem body in Control Group 2.
Figure 16:
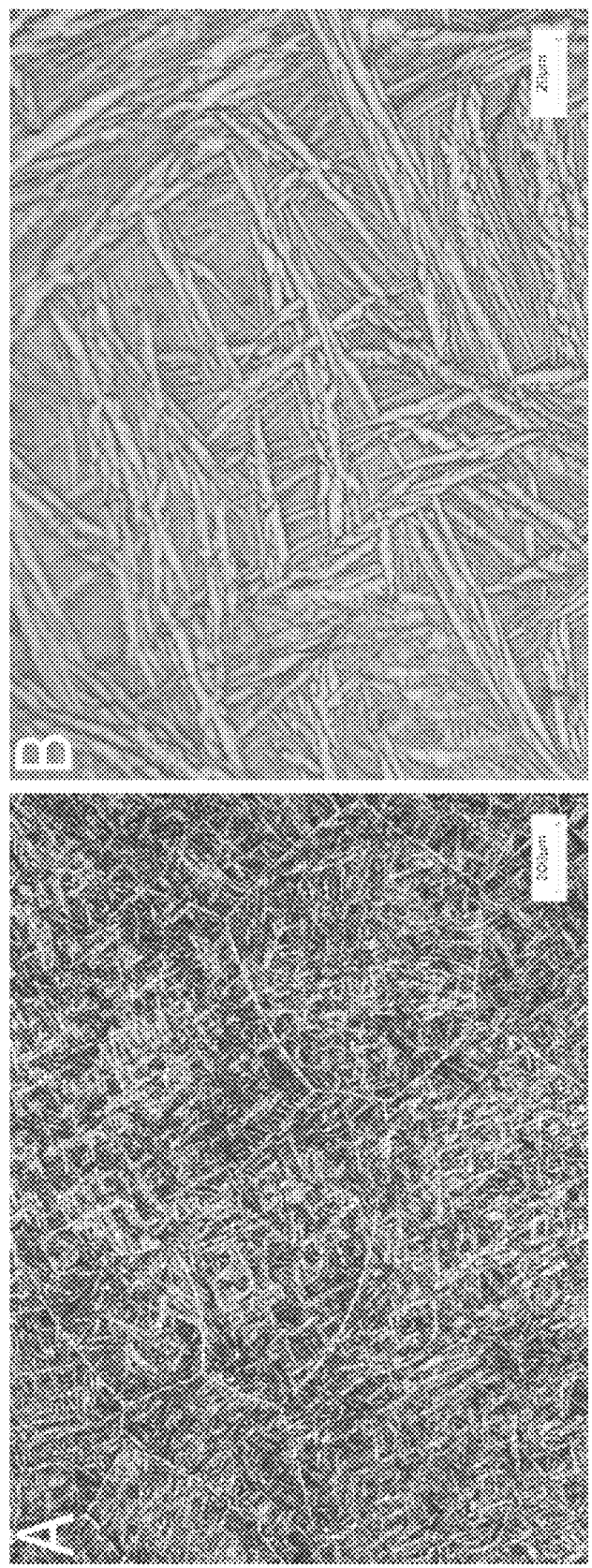
FIG. 16 shows the metallographic microscopic structure of the body of the femoral stem in Embodiment 1 that has not been prepared with step 1-4) and step 1-5) in the preparation method.

A solid part of the femoral stem in the control group 2 and a femoral stem of the embodiment 1 that has not been prepared with step 1-4) and 1-5) were observed and analyzed by an inverted scanning electron microscope (Axio Vert.A1, Zeiss, Germany). The results were shown in FIGS. 15-16. In the metallographic photos of the Control Group 2, small a martensite can be observed. The structure is small, easy for stress concentration, and the plasticity is poor. In the metallograph of Embodiment 1, a phase can be observed, basket net structure, grain refinement. The results indicated that the femoral stem solid part (without oxidation layer) of the hip prosthesis of the present disclosure has excellent strength and plasticity.

Figure 17:
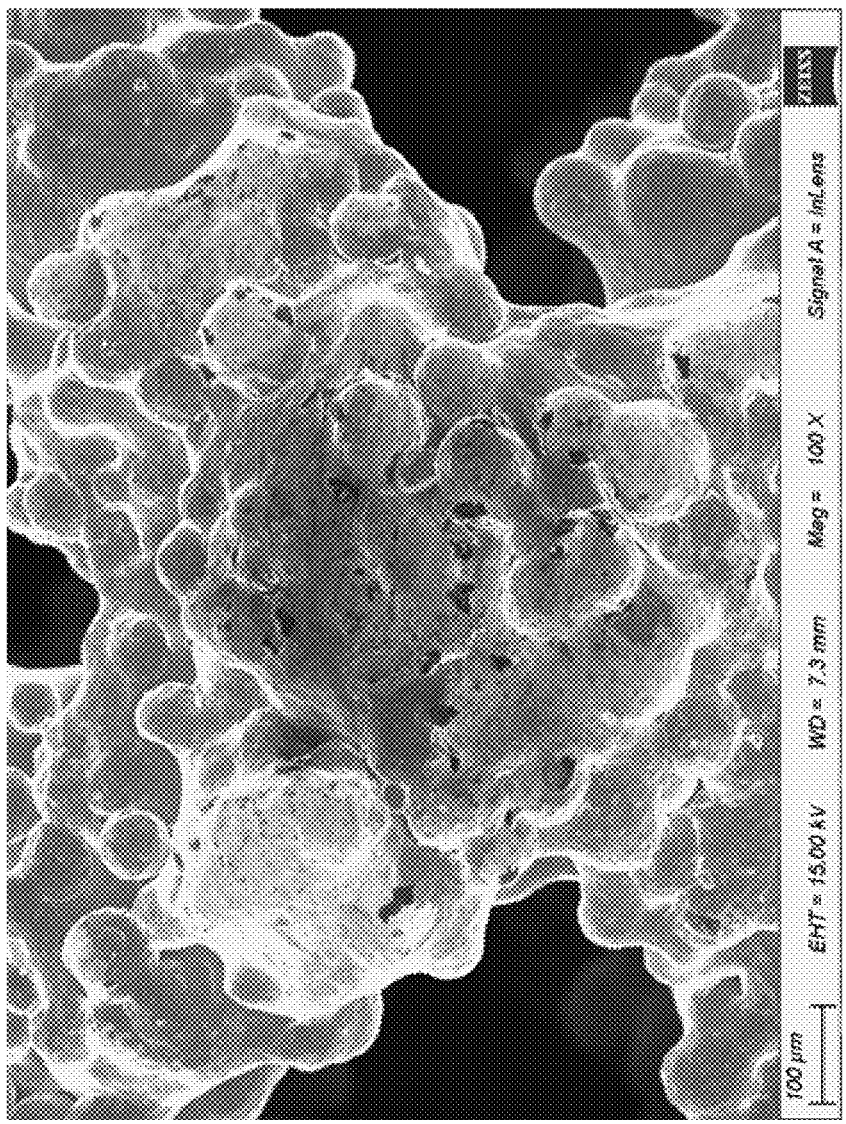
FIG. 17 shows the femoral stem trabeculae SEM of Control Group 2.
Figure 18:
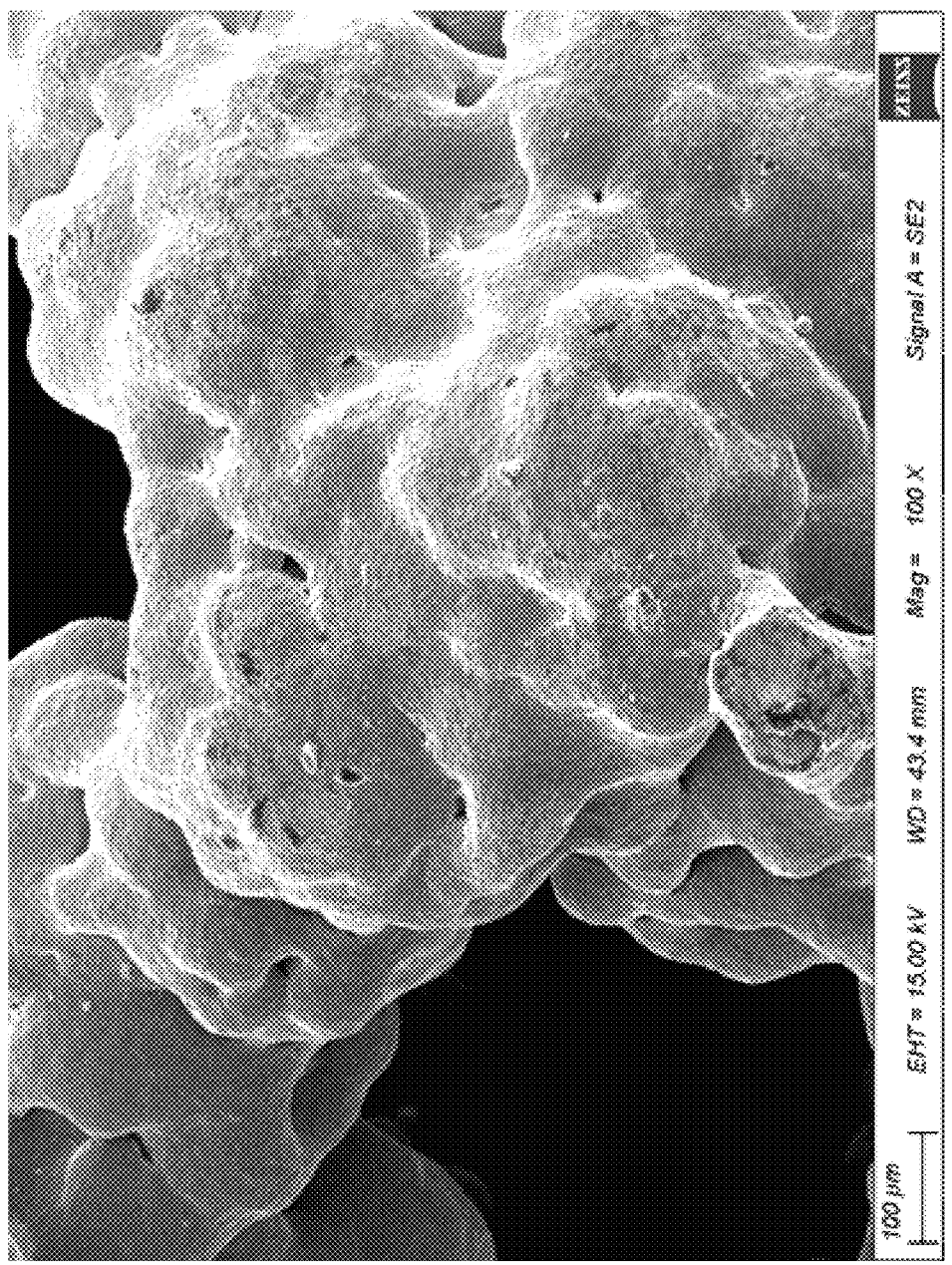
FIG. 18 shows the trabeculae SEM diagram of femoral stem in Embodiment 1 that has not been prepared with step 1-4) and step 1-5) of the preparation method.

A trabecula part of the femoral stem in the control group 2 and a femoral stem of the embodiment 1 that has not been prepared with step 1-4) and 1-5) were observed and analyzed by scanning electron microscope (Axio Vert.A1, Zeiss, Germany). The results were shown in FIGS. 17-18. Compared with the Control Group 2, the zirconium-niobium alloy powder in the bone trabecular structure of Embodiment 1 was further sintered, indicating that a combination property of the bone trabeculae was improved.

A physical compression test piece (size: 8*8*10 mm$^3$) of the femoral stem according to the preparation method that has not been prepared with step 1-4) and 1-5) in the embodiment 1 and a physical compression test piece (size: 8*8*10 mm$^3$) of the femoral stem in the control group 2 were subjected to a compression performance test by an electronic universal testing machine (UTM5105, Shenzhen SUNS Technology Co., Ltd., and China). There were 5 physical compression test pieces respectively in the embodiment 1 and the control group 2. Results were shown in Table 1. The compressive yield strength of embodiment 1 is 546.72 MPa, better than that of Control Group 2 (P<0.05), suggesting that the solid part of the femoral stem prepared by the present disclosure has excellent anti-compression performance.

TABLE 1

Anti-compression experiment results of the solid specimens of Control Group 2 and Embodiment 1 ($\bar{x} \pm$ s, n = 5, *P < 0.05, compared with Control Group 2)

| Group | Cross-sectional Area (mm$^2$) | Yield Load (kN) | Yield Strength (MPa) |
|---|---|---|---|
| Embodiment 1 | 64 | 34.99 ± 4.04* | 546.72 ± 63.19* |
| Control Group 2 | 64 | 23.59 ± 2.30 | 368.63 ± 35.92 |

A bone trabecular compression specimens of the femoral stem with pore size of 780 μm and porosity of 76% of the Control Group 2 and the bone trabecular compression specimens of the femoral stem with pore size of 780 μm and porosity of 76% of Embodiment 1 (specimen size: 8*8*10 mm$^3$) that has not been prepared with step 1-4) and step 1-5) of the above-mentioned preparation method, were subjected to a compression test by the electronic universal testing machine (UTM5105, Shenzhen SUNS Technology Co., Ltd., and China). Bone trabecular compression specimens of the Control Group 2 and the Embodiment 1 were 5 pieces each. The results are shown in Table 2. The compressive yield strength of Embodiment 1 is 17.94 MPa, significantly better than that of Control Group 2 (P<0.05), suggesting that the bone trabecular part of the femoral stem prepared by the present disclosure has excellent anti-compression performance.

TABLE 2

Anti-compression experiment results of the bone trabecular specimens of Control Group 2 and Embodiment 1 ($\bar{x} \pm$ s, n = 5, *P < 0.05, compared with Control Group 1)

| Group | Cross-sectional Area (mm$^2$) | Yield Load (N) | Yield Strength (MPa) |
|---|---|---|---|
| Embodiment 1 | 64 | 1148.19 ± 116.43* | 17.94 ± 1.82* |
| Control Group 2 | 64 | 848.05 ± 96.67 | 13.25 ± 1.51 |

Figure 19:
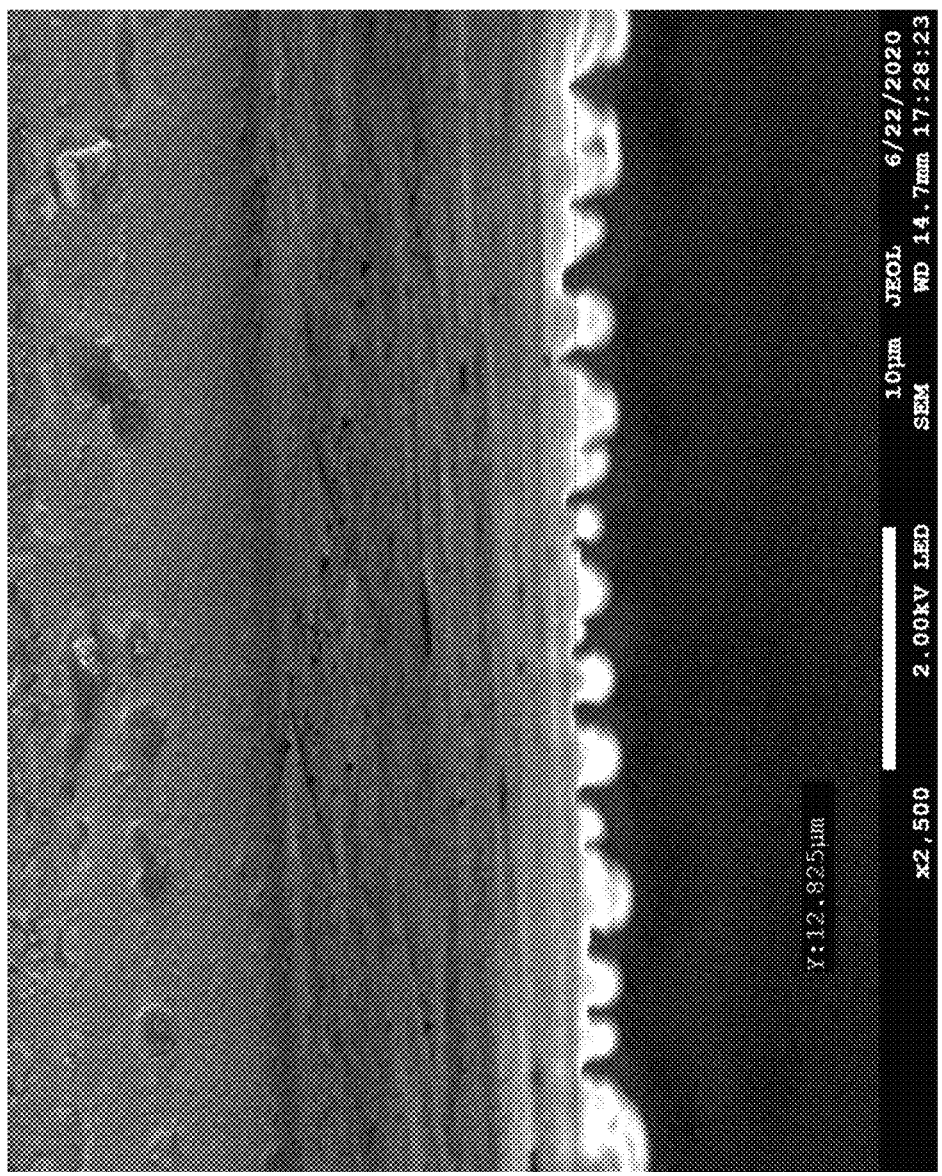
FIG. 19 shows the SEM of cross section of femoral stem oxidation layer and matrix in Embodiment 1.

The cross-section of the matrix and oxidation layer of the zirconium-niobium alloy of the femoral stem in Embodiment 1 was observed by scanning electron microscopy (Crossbeam340/550, Zeiss, Germany) (see FIG. 19). The cross sections of the matrix and oxidation layer of the zirconium-niobium alloy of femoral stem in Embodiments 2 and 3 were observed. The oxidation layer thickness were 10.3 μm, 17.2 μm and 20.6 μm, respectively. There was an oxygen-rich layer between the oxidation layer and the matrix of the zirconium-niobium alloy to enhance the bonding force between the matrix and oxidation layer of zirconium-niobium alloy.

Figure 20:
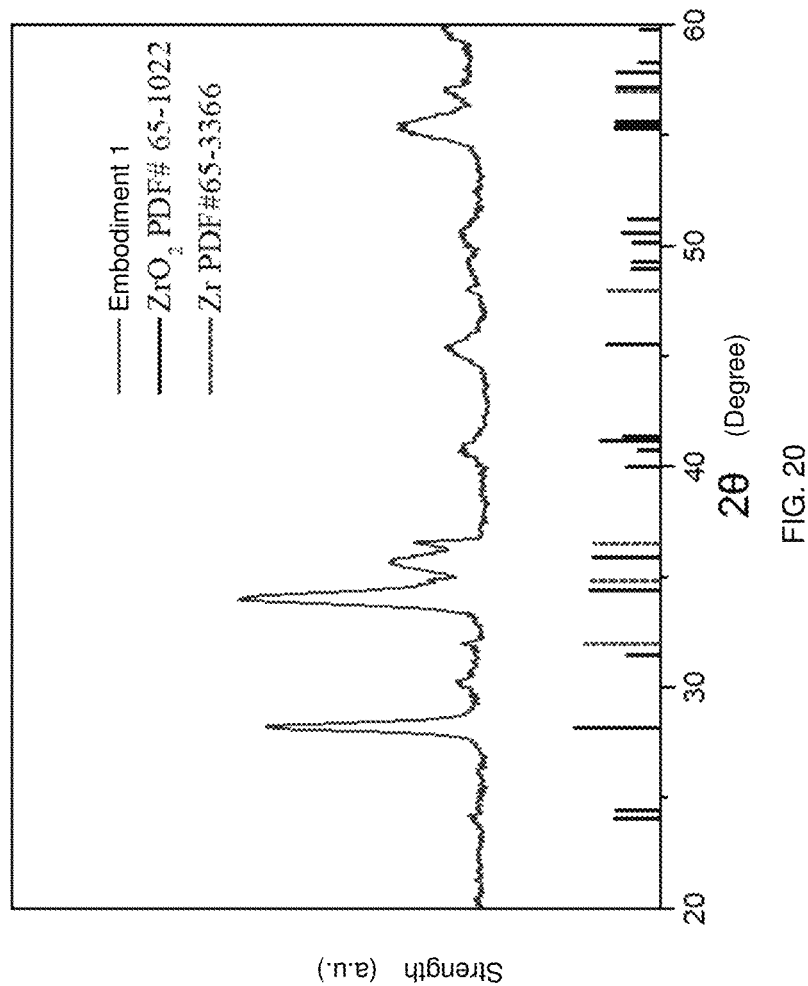
FIG. 20 shows the XRD curve of oxidation layer surface of the femoral stem in Embodiment 1.

XRD (D8DISCOVER, Bruker, Germany) analyzed the oxidation layer of the femoral stem of Embodiment 1 (FIG. 20). The oxidation layer contained monoclinic phase zirconia and tetragonal phase zirconia.

The microhardness measurement on the femoral stem of Embodiments 1-3 was determined by a microhardness tester (MHVS-1000 PLUS, Shanghai Aolongxingdi Testing Equipment Co., Ltd., China), in which the load was 0.05 kg, the load time of the specimens was 20 s, and 8 points were taken for each specimen. The average hardness values measured in Embodiments 1-3 were 1948.6Hv, 1923.7Hv, and 1967.2Hv, suggesting that the stem oxidation layer in the hip prosthesis of the present disclosure has high hardness.

Experiments have proved that the zirconium-niobium alloy powder bonding degree, compressive properties, solid part of the compressive properties, metallographic structure, the crystal structure, thickness and hardness of the oxidation layer for the shell and femoral stem prepared in Embodiments 2 and 3 and the shell prepared in Embodiment 1, are similar to that femoral stem prepared in Embodiment 1. The crystal structure, thickness and hardness of the oxide layers of femoral head and liners prepared in Embodiments 1, 2 and 3 are similar to those of femoral stem prepared in Embodiment 1.

The invention claimed is:

1. A preparation method of a hip prosthesis containing zirconium-niobium alloy on oxidation layer comprising the following steps:
   1) Preparation of shell and femoral stem:
   1-1) using zirconium-niobium alloy powder as a raw material, conducting a 3D printing for one-piece molding, and obtaining a first intermediate of shell and a first intermediate of femoral stem respectively, putting the two first intermediates into the Sinter-HIP furnace, heating to 1250° C.-1400° C. under helium/argon gas protection, placing at a constant pressure of 140 MPa-180 MPa for 1 h to 3 h, reducing to atmospheric pressure, cooling to below 200° C. with the furnace, taking them out, and obtaining a second intermediate of the shell and a second intermediate of the femoral stem;
   1-2) placing two second intermediate products in a programmable cooling box to cool to −80° C. to −120° C. at a rate of 1° C./min, keeping them at a constant temperature for 5 h to 10 h, and taking them out of the programmable cooling box; placing them in a liquid nitrogen for 16 h to 36 h, and adjusting the temperature to room temperature so as to obtain a third intermediate of the shell and a third intermediate of the femoral stem;
   1-3) placing two third intermediate products in the programmable cooling box to cool to −80° C. to −120° C. at a rate of 1° C./min, and placing them at a constant temperature for 5 h to 10 h, taking them out of the programmable cooling box, placing them in the liquid nitrogen for 16 h to 36 h and adjusting the temperature to room temperature so as to obtain a fourth intermediate of the shell and a fourth intermediate of the femoral stem;
   1-4) machining, finishing, polishing, cleaning, and drying the fourth intermediate products, and obtaining a fifth intermediate of the shell and a fifth intermediate of the femoral stem;
   1-5) placing the two fifth intermediate products in a tube furnace, introducing helium/argon gas containing 5% to 15% of oxygen in percentage by mass, heating to 500° C. to 700° C. at 5° C./min to 20° C./min, and cooling down to 400° C. to 495° C. at 0.4° C./min to 0.9° C./min; and cooling to be below 200° C. sequentially, taking them out to obtain the shell and femoral stem;
   2) Preparation of liners and femoral head:
   2-1) machining, finishing, polishing, cleaning, and drying forged pieces containing zirconium-niobium alloy to obtain the intermediate products of liners or femoral head; the roughness of the inner and outer surfaces of the intermediate products of liners is Ra≤0.050 μm; the outer surface roughness of the intermediate products of femoral head is Ra≤0.050 μm;
   2-2) placing the intermediate products of liners and femoral head in a tube furnace, introducing helium/argon gas containing 5% to 15% of oxygen in percentage by mass, heating to 500° C. to 700° C. at 5° C./min to 20° C./min, and cooling to 400° C. to 495° C. at 0.4° C./min to 0.9° C./min; and natural cooling to be below 200° C. sequentially, taking them out to obtain the liners and femoral head;
   the hip prosthesis containing zirconium-niobium alloy on oxidation layer comprises a femoral stem (1), a femoral head (2), liners (3) and a shell (4);
   the femoral stem comprises a cylindrical head (11), a neck (12) and a hilt (13); the hilt (13) comprises a proximal hilt (14) and a distal hilt (15); a stem trabeculae (16) is arranged on the outer surface of the proximal hilt (14), the stem trabeculae (16) is partitioned into a lateral upper zone (1101), a lateral lower zone (1102), a medial upper zone (191) and a medial lower zone (192); the trabeculae arranged in the lateral upper zone 1101 and medial lower zone (192) are a first trabeculae (112); a trabeculae arranged in the medial upper zone 191 is a second trabeculae (113); a trabeculae arranged in the lateral lower zone (1102) is a third trabeculae (114); the pore size and porosity of the first trabeculae (112) are sequentially smaller than that of the second trabeculae (113) and the third trabeculae (114);
   the structure of the shell is the same as its first intermediate, second intermediate, third intermediate, fourth intermediate and fifth intermediate;
   the structure of the femoral stem is the same as its first intermediate, second intermediate, third intermediate, fourth intermediate, and fifth intermediate;
   the shell comprises a hemispherical body (49), the middle part of which is provided with a first circular hole (41) with internal thread, and the outer surface of the hemispherical body is provided with a shell trabeculae (43), which is partitioned setting; a first partition line (46) intersects with a second partition line (45); the intersection point crosses the center of the first circular hole (41), and a third partition line (44) has circular shape and is located near the edge of the hemispherical body (49); the first, second and third partition lines divide the outer surface of the hemispherical body into a first upper region (471), a first lower region (472), a second upper region (473), a second lower region (474), a third upper region (475), a third lower region (476), a fourth upper region (477) and a fourth lower region (478); the area of the first upper region, the second upper region, the third upper region and the fourth upper region is equal; 3 second round holes (42) with internal thread are arranged on one side of the hemispherical body, two of which are respectively arranged in the first upper region (471) and the third upper region (475), and another is arranged in the junction of the first upper region (471) and the third upper region (475);

a fourth trabeculae (481) is arranged on the third upper region and fourth upper region respectively;

a fifth trabeculae (482) is arranged on the third lower region and fourth lower region respectively;

a sixth trabeculae (483) is arranged on the first upper region;

a seventh trabeculae (484) is arranged on the first lower region;

an eighth trabeculae (485) is arranged on the second upper region;

a ninth trabeculae (486) is arranged on the second lower region;

the pore size and porosity of the fourth trabeculae are sequentially smaller than that of the fifth trabeculae, the sixth trabeculae, the seventh trabeculae, the eighth and the ninth trabeculae.

2. The preparation method according to claim 1, wherein the chemical composition of the zirconium-niobium alloy powder in percentage by mass is respectively 85.6%-96.5% of Zr, 1.0%-12.5% of Nb, and the rest are unavoidable impurities; where a particle size of the zirconium-niobium alloy powder ranges from 45 to 150 µm.

3. The preparation method according to claim 1, wherein the chemical composition of the forged pieces of zirconium-niobium alloy in percentage by mass includes 85.6%-96.5% of Zr and 1.0%-12.5% of Nb, and the residual is unavoidable impurities.

4. The preparation method according to claim 1, wherein the specific steps for adjusting the temperature in steps 1-2) and 1-3) are: increasing the temperature to −120° C. to −80° C. and keeping the constant temperature for 3 h to 5 h; then increasing the temperature to −40° C. to −20° C. and keeping the constant temperature for 3 h to 5 h and then increasing the temperature to 4° C. to 8° C. and keeping the constant temperature for 1 h to 3 h and then increasing the temperature.

5. The preparation method according to claim 1, wherein the pore size of the first trabeculae (112) ranges from 700 µm to 770 µm, and the porosity ranges from 65% to 75%;

the second trabeculae (113) has pore size ranging from 780 µm to 850 µm and porosity ranging from 76% to 80%;

the third trabeculae (114) has pore size ranging from 860 µm to 950 µm and porosity ranging from 81% to 85%;

the thickness of the first trabeculae, the second trabeculae and the third trabeculae are equal to 1.2 mm to 1.5 mm;

the fourth trabeculae (481) has pore size ranging from 700 µm to 740 µm and porosity ranging from 65% to 70%;

the fifth trabeculae (482) has pore size of 750 µm to 770 µm and porosity ranging from 71% to 75%;

the sixth trabeculae (483) has pore size ranging from 780 µm to 810 µm and porosity ranging from 76% to 78%;

the seventh trabeculae (484) has pore size ranging from 820 µm to 850 µm and porosity ranging from 79% to 80%;

the eighth trabeculae (485) has pore size ranging from 860 µm to 900 µm and porosity ranging from 81% to 83%;

the ninth trabeculae (486) has pore size ranging from 910 µm to 950 µm and a porosity ranging from 84% to 85%;

the fourth trabeculae, fifth trabeculae, sixth trabeculae, seventh trabeculae, eighth trabeculae and ninth trabeculae have the same thickness of 1.2 mm to 1.5 mm.

6. The hip prosthesis containing zirconium-niobium alloy on oxidation layer prepared by the preparation method according to claim 1.

7. The hip prosthesis containing zirconium-niobium alloy on oxidation layer prepared by the preparation method according to claim 2.

8. The hip prosthesis containing zirconium-niobium alloy on oxidation layer prepared by the preparation method according to claim 3.

9. The hip prosthesis containing zirconium-niobium alloy on oxidation layer prepared by the preparation method according to claim 4.

10. The hip prosthesis containing zirconium-niobium alloy on oxidation layer prepared by the preparation method according to claim 5.

* * * * *